United States Patent [19]

Ten Haken et al.

[11] 4,304,789
[45] Dec. 8, 1981

[54] BENZOIN OXIME FUNGICIDES

[75] Inventors: Pieter Ten Haken, Eastling; Robert F. Appleton; Brian P. Armitage, both of Sittingbourne, all of England

[73] Assignee: Shell Oil Company, Houston, Tex.

[21] Appl. No.: 110,973

[22] Filed: Jan. 10, 1980

Related U.S. Application Data

[63] Continuation-in-part of Ser. No. 41,980, May 24, 1979, abandoned.

[30] Foreign Application Priority Data

Jun. 8, 1978 [GB] United Kingdom ............... 26530/78
May 23, 1979 [EP] European Pat. Off. ......... 79200255.2

[51] Int. Cl.³ ..................... A01N 33/24; A01N 33/26
[52] U.S. Cl. .................................................. 424/327
[58] Field of Search .................. 260/566 A, 566 AE; 424/327

[56] References Cited

U.S. PATENT DOCUMENTS

| | | | |
|---|---|---|---|
| 3,920,842 | 11/1975 | Peronnet et al. | 424/327 |
| 3,992,538 | 11/1976 | Teufel et al. | 424/327 |
| 4,052,194 | 10/1977 | Wilcox | 71/121 |
| 4,059,625 | 11/1977 | Baker et al. | 260/566 AE |

OTHER PUBLICATIONS

Fischer, E., Chemische Berichte, vol. 26, pp. 2413–2414 (1893).

*Primary Examiner*—Leonard Schenkman

[57] ABSTRACT

Unwanted fungi are controlled by the use of certain benzoin oximes.

1 Claim, No Drawings

BENZOIN OXIME FUNGICIDES

This application is a continuation-in-part of application Ser. No. 041,980, filed on May 24, 1979 now abandoned.

DESCRIPTION OF THE INVENTION

This invention relates to the use of certain benzoin oximes for the control of unwanted fungi, these oximes being described by the formula:

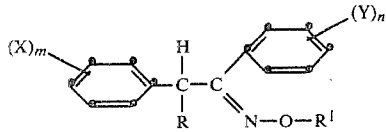

wherein:

(a) m is zero or one, n is one, X and Y each is middle halogen or alkyl of one to four carbon atoms bonded to a carbon atom in the meta- or para-position in the ring, R is methoxy and $R^1$ is hydrogen, methyl or acetyl;

(b) m, n, X and Y are as defined in (a), R is ethoxy, and $R^1$ is hydrogen;

(c) m is one, n is zero, X is middle halogen, R is as defined in (a) and $R^1$ is hydrogen;

(d) m is one, X is as defined in (a), n is zero, R is as defined in (a) and $R^1$ is hydrogen, the compound being in the Z isomeric configuration;

(e) m is zero, n is zero or one, Y is as defined in (a), R is alkylthio of one or two carbon atoms, and $R^1$ is hydrogen.

By "middle halogen" is meant chlorine and bromine. The alkyl moieties represented by X and Y suitably are of either straight-chain or branched-chain configuration.

Being oximes, the compounds of Formula I exist as geometric (i.e., E and Z) isomers. Further, due to the presence of an asymmetric carbon atom, chirality exists, and the compounds can exist in the form of optical isomers. Except in the case of the compounds of subclass (c), Formula I, both of the geometric forms have been found to be fungicidal. The relative activities of the individual optical isomers has not been determined. The invention contemplates all of the active isomers, as well as mixtures thereof.

Compounds of Formula I can be prepared by converting a benzyl phenyl ketone A,

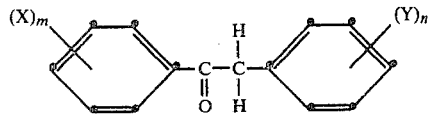

to a compound, B,

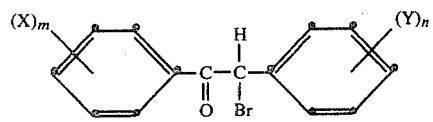

by reaction with bromine in the presence of a suitable solvent such as carbon tetrachloride, under the influence of light radiation, and then, after reaction with an alkoxide compound, usually a mixture of an alkali metal alcoholate and the corresponding alcohol, which is preferably the methoxide and methanol, converted by pyrolysis preferably at a temperature in the range of 160°–200° C. In this reaction a reversal of the position of the >CO group with respect to the aromatic rings occurs to form a compound, C:

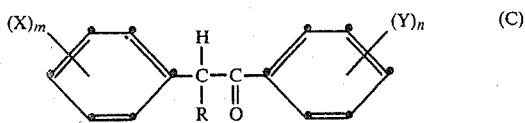

By reaction with hydroxylamine the oximes are obtained, from which further oxime derivatives may be prepared if so desired.

Alternatively the oximes may be prepared by reaction of the compounds of formula D:

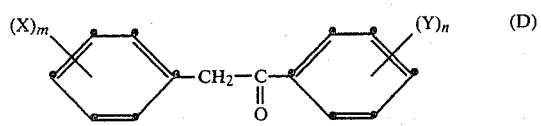

with bromine, in the manner as described above and then either by direct reaction with an alcohol, or, after replacing the bromine atom by a hydroxyl group, suitably by a treatment with an alcoholic solution of an alkali metal alcoholate followed by a treatment with diluted acid, suitably HCl, by conversion of the benzoin thus obtained with an alkyl iodide and silver oxide dissolved in an alkyl ester such as ethyl acetate and subsequent reaction with hydroxylamine to the corresponding oxime.

The compound of formulae A and D are conveniently prepared by a Grignard reaction or by a reaction catalyzed by a Lewis acid such as aluminum chloride.

The compounds of formula C may also be prepared via benzoins of the formula E:

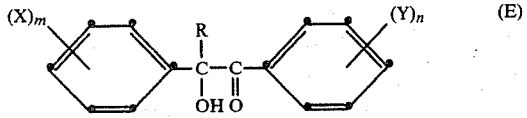

which benzoins can be prepared by coupling of monoaromatic compounds by any suitable technique, such as aldol condensation—e.g., by refluxing aromatic aldehydes in the presence of potassium cyanide and an alcohol, or in the presence of a substituted thiazolium halide.

The invention is further illustrated by the following Examples. In each case, the identity of the product was confirmed by appropriate chemical and spectral analyses.

EXAMPLE 1

4-chlorobenzoin O-methylether (E)-oxime (1)

50.6 g of dry benzyl chloride in 200 ml of dry ether was treated with 10 g of magnesium. When the reaction was complete, 15.6 g of 4-chlorobenzamide was added in portions with stirring. When the addition was complete the mixture was stirred and refluxed for 65 hours. The cooled mixture then was poured onto 400 g of ice containing 40 g of concentrated sulphuric acid. Several extractions with ether yielded the crude product as a white solid. Recrystallization from methylated spirit gave white crystals of 4-chlorodeoxybenzoin, 1A, mp: 106°–106.5° C.

138 g of 1A was suspended in 800 ml of carbon tetrachloride. A solution of 96 g of bromine in carbon tetrachloride was added dropwise while a strong light was shown on the reaction vessel to initiate the reaction. When the reaction was complete the solvent and dissolved gases were removed under reduced pressure to give bromo-4-chlorodeoxybenzoin, 1B, as a pale yellow solid, mp: 67°–67.5° C.

146.5 g of 1B was dissolved in 800 ml of ethanol at 30°–35° C. This solution was added to a solution of 38 g of sodium in 750 ml of ethanol and stirred overnight at room temperature. The mixture was poured into 3 liters of iced water containing 350 ml of concentrated hydrochloric acid. The resulting pale yellow solid was filtered, washed with water and dried to yield 4-chlorobenzoin, 1C, mp: 89°–90° C.

2.47 g of 1C was dissolved in 10 ml of dry ethyl acetate. To this solution was added 2.31 g of freshly prepared dry silver oxide and 7.1 g of dry methyl iodide. The stirred mixture was heated at 50° C. for 3 hours. Filtration, followed by evaporation of solvents yielded a yellow oil, which slowly solidified to give 4-chlorobenzoin O-methyl ether, 1D, as a yellow solid, mp: 37°–39° C.

87.7 g of 1D was dissolved in 350 ml of ethanol and treated with a solution of 112 g of potassium hydroxide and 69.5 g of hydroxylamine hydrochloride in 400 ml of water at 25° C. After 2 hours, the mixture was poured into 2 liters of cold water. Extraction with ether yielded a brown oil, which upon trituration with petroleum ether gave 1, as a pale yellow solid, mp: 103°–105° C.

EXAMPLE 2

4-fluorobenzoin O-methylether (E) and (Z) oximes (2 and 3, respectively)

28.4 g of phenylacetyl chloride was dissolved in 130 ml of fluorobenzene and cooled in ice. This solution was added to 27.0 g of freshly powdered aluminum chloride with continued cooling and stirring. After the vigorous reaction subsided, the mixture was stirred at room temperature overnight and then poured onto 150 g of ice containing 50 ml of concentrated hydrochloric acid. Extraction gave a pale brown solid. Recrystallization from petroleum ether gave 4-fluorodeoxybenzoin, 2A, as a white solid, mp: 80°–81° C.

2A was converted to 4-fluorobenzoin O-methylether, 2B, via bromo-4-fluorodeoxybenzoin and 4-fluorobenzoin by procedures analogous to those described in Example I. 4.5 g of 2B was warmed at 50° C. for 3 hours with a mixture of 4.8 g of potassium acetate and 3.0 g of hydroxylamine hydrochloride in 80 ml of ethanol. After cooling and pouring into cold water, ether extraction resulted in the isolation of a yellow oil. The two oxime isomers contained therein were separated by silica gel column chromatography, eluting with methylene chloride. The Z-isomer, 3, was recovered first as a pale yellow solid, mp: 93°–97° C., followed by the E-isomer, 2, as a white solid, mp: 81°–82° C.

EXAMPLE 3

4-chlorobenzoin O-methylethylether oxime (Z) (4)

4, mp: 108°–111° C., was prepared by the general procedures described in Example 1.

EXAMPLE 4 acetyl 4-chlorobenzoin O-methylether oxime (Z) (5)

3.4 g of 4 was dissolved in 35 ml of dry methylene chloride and treated with 1.0 g of acetyl chloride in the presence of 2.5 ml of triethylamine. The mixture was stirred for 2 hours at room temperature, then poured into water. The organic layer was separated, washed with water, dried and the solvent was evaporated under reduced pressure to yield 5, as a pale brown oil.

EXAMPLE 5

4,4'-difluorobenzoin O-methylether (E) and (Z) oximes (6 and 7)

A mixture of 36.4 g of fluorobenzaldehyde, 5.0 g of triethylamine and 1.0 g of 3-ethyl-5-(2-hydroxyethyl)-4-methyl thiazolium bromide catalyst was refluxed overnight in 100 ml of ethanol. The mixture was cooled, poured into water and the crude product filtered. Recrystallization from methylated spirit gave, 4,4'-difluorobenzoin, 6A, as white crystals, mp: 82°–83° C.

By the general procedures described in Example 1, 6A was converted into 6 mp: 96°–99° C., and 7, mp: 91°–94° C.

EXAMPLES 6–27

Following procedures similar to those described in the previous Examples, a number of other oximes were prepared as indicated in Table I.

TABLE I

| Example No. | Compound No. | Compound | Melting Point (°C.) |
|---|---|---|---|
| 6 | 8 | 4'-chlorobenzoin O-methyl ether oxime (E) | 78–80 |
| 7 | 9 | 4'-chlorobenzoin O-methylether oxime (Z) | 127–130 |
| 8 | 10 | 4,4'-dichlorobenzoin O-methylether oxime (Z) | 99–100 |
| 9 | 11 | 4,4'-dichlorobenzoin O-methylether oxime (E) | 138–140 |
| 10 | 12 | methyl 4-chlorobenzoin O-methylether oxime (E) | oil |
| 11 | 13 | methyl 4-chlorobenzoin O-methylether oxime (Z) | 74–76 |
| 12 | 14 | 4-chlorobenzoin O-ethyl-ether oxime (E) | 110–113 |
| 13 | 15 | 4-chlorobenzoin O-ethyl-ether oxime (Z) | oil |
| 14 | 16 | acetyl 4-chlorobenzoin O-methylether oxime (E) | oil |
| 15 | 17 | 4,4'-dimethylbenzoin O-methylether oxime (E) | 147–153 |
| 16 | 18 | 4,4'-dimethylbenzoin O-methylether oxime (Z) | 119–122 |
| 17 | 19 | 3-chlorobenzoin-O-methylether oxime (E) | 94.5–95.5 |
| 18 | 20 | 3-chlorobenzoin-O-methylether oxime (Z) | 87–90 |
| 19 | 21 | acetyl-4-fluorobenzoin-O-methylether oxime (Z) | oil |
| 20 | 22 | acetyl-3-chlorobenzoin-O-methylether oxime (Z) | oil |
| 21 | 23 | 4-bromobenzoin-O-methylether oxime (E) | 101–103 |
| 22 | 24 | 4-bromobenzoin-O-methylether oxime (Z) | 114–117 |
| 23 | 25 | benzoin-S-methylthioether oxime (Z) | 104–105 |
| 24 | 26 | 4-methylbenzoin-O-methylether oxime (E) | 115–118 |
| 25 | 27 | 4-methylbenzoin-O-methyl ether oxime (Z) | 103–105 |
| 26 | 28 | 4'-methylbenzoin-O-methyl- | 86–89 |

TABLE I-continued

| Example No. | Compound No. | Compound | Melting Point (°C.) |
|---|---|---|---|
| 27 | 29 | ether oxime (Z) 4'-chlorobenzoin-S-methylthio-ether oxime (Z) | 105-106 |

All structures, configurations and purities are supported by NMR spectroscopic data.

EXAMPLE 28

Fungicidal Activity

The fungicidal activity of the compounds according to the invention was investigated by the following foliar spray tests:

(1) Activity against vine downy mildew (Plasmorpara viticola - Pv.a)

The test was a direct antisporulant one using a foliar spray. The lower surface of leaves of whole vine plants are inoculated by spraying with an aqueous suspension containing $10^5$ zoosporangia per milliliter four days prior to treatment with the test compound. The inoculated plants were kept for 24 hours in a high humidity compartment, 48 hours at glasshouse ambient temperature and humidity and then returned for a further 24 hours to high humidity. The plants then were dried and infected leaves detached and sprayed on the lower surfaces at a dosage of 1 kilogram of active material per hectare using a track sprayer. After drying, the petioles of the sprayed leaves were dipped in water and the leaves returned to high humidity for a further 72 hours incubation, followed by assessment. Assessment was based on the percentage of the leaf area covered by sporulation compared with that on control leaves.

(2) Activity against vine downy mildew (Plasmopara viticola - Pv.t)

The test was a translaminar protectant one using a foliar spray. The upper surfaces of leaves of whole vine plants were sprayed at a dosage of 1 kilogram of active material per hectare using a track sprayer. The lower surfaces of the leaves were then inoculated, up to 6 hours after treatment with the test compound, by spraying with an aqueous suspension containing $10^5$ zoosporangia per milliliter. The inoculated plants were kept for 24 hours in a high humidity compartment, 4 days at glasshouse ambient temperature and humidity and then returned for a further 24 hours to high humidity. Assessment was based on the percentage of the leaf area covered by sporulation compared with that on control leaves.

(3) Activity against barely powdery mildew (Erysiphe graminis - Eg.)

The test measured the direct antisporulant activity of compounds applied as a foliar spray. For each compound about 40 barely seedlings were grown to the one-leaf stage in a plastic pot of sterile potting compost. Inoculation was effected by dusting the leaves with conidia of *Erysiphe graminis*. spp. hordei. 24 hours after inoculation the seedlings were sprayed with a solution of the compound in a mixture of acetone (50%), surfactant (0.049%) and water using a tract sprayer. The rate of application was equivalent to 1 kilogram of active material per hectare. First assessment of disease was made 5 days after treatment, when the overall level of sporulation on the treated pots were compared with that on control pots.

(4) Activity against potato late blight (Phytophthora infestans - Pi.p)

The test measured the direct protectant activity of compounds applied as a foliar spray. Tomato plants, cultivar Ailsa Craig, 1-15 cms high, in monopots were used. The whole plant was sprayed at a dosage of 1 kilogram of active material per hectare using a track sprayer. The plant then was inoculated up to 6 hours after treatment with the test compound, by spraying with an aqueous suspension containing $5 \times 10^3$ zoosporangia per milliliter. The inoculated plants were kept in high humidity for 3 days. Assessment was based on a comparison between the levels of disease on the treated and control plants.

The extent of disease control was expressed as a control rating according to the criteria:
0 = less than 50% disease control
1 = 50-80% disease control
2 = greater than 80% disease control The disease control ratings are given in Table II for the compounds described in the previous Examples.

TABLE II

| Compound No. | Pv.a | Pv.t | Eg. | Pi.p |
|---|---|---|---|---|
| 1 | 2 | 2 | 0 | 2 |
| 2 | 2 | 2 | 0 | 2 |
| 3 | 2 | 2 | 0 | 2 |
| 4 | 2 | 2 | 2 | 0 |
| 5 | 2 | 2 | 2 | 2 |
| 6 | 1 | 2 | 0 | 1 |
| 7 | 2 | 2 | 0 | 2 |
| 8 | 1 | 2 | 0 | 1 |
| 9 | 0 | 1 | 0 | 2 |
| 10 | 0 | 2 | 0 | 1 |
| 11 | 2 | 0 | 0 | 2 |
| 12 | 0 | 0 | 2 | 0 |
| 13 | 2 | 2 | 0 | 0 |
| 14 | 0 | 2 | 0 | 1 |
| 15 | 2 | 2 | 0 | 2 |
| 16 | 2 | 2 | 1 | 0 |
| 17 | 1 | 0 | 2 | 2 |
| 18 | 2 | 2 | 2 | 2 |
| 19 | 2 | 2 | 1 | 2 |
| 20 | 2 | 2 | 2 | 2 |
| 21 | 2 | 2 | 2 | 2 |
| 22 | 2 | 2 | 2 | 2 |
| 23 | 1 | 1 | 0 | 2 |
| 24 | 2 | 2 | 1 | 2 |
| 25 | 0 | 0 | 0 | 2 |
| 26 | 2 | 2 | 0 | 1 |
| 27 | 2 | 2 | 1 | 2 |
| 28 | 2 | 0 | 0 | 2 |
| 29 | 2 | 2 | 0 | 1 |

The invention includes the compounds of Formula I, per se, fungicidal compositions containing them, and their use for protecting crops from attack by fungi, in which crops subject to or subjected to such attack, seeds of such crops or soil in which such crops are growing or to be grown are treated with a fungicidally effective amount of at least one of the compounds of Formula I, preferably in the form of a composition together with a carrier, with a surface-active agent or both a carrier and a surface active agent.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols;bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-ctive agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspensing agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may contain other ingredients, for example, protective colloids such as gelatin, glue, casin, gums, cellulose ethers, and polyvinyl alcohol; thioxtropic agents, e.g., bentonites, sodium polyphosphates; stabilizers such as ethylene diamine tetra-acetic acid, urea, triphenyl phosphate; other fungicides or pesticides; and stickers, for example nonvolatile oils.

The compositions of the invention may also contain other biologically active ingredients, for example, other compounds possessing pesticidal, especially insecticidal, acaricidal, herbicidal or fungicidal properties.

The method of applying the compounds of this invention comprises applying a compound of Formula I, ordinarily in a composition of one of the aforementioned types, to a locus or area to be protected from undesirable fungi, such as the foliage of the plants or the plant growth medium, e.g., soil in which the plant is growing or is to be grown. The active compound, of course, is applied in amounts sufficient to exert the desired action.

The amount of compound of the invention to be used in controlling undesirable fungi will naturally depend on the fungi that are involved, the formulation used, the mode of application, the climate, the season of the year, and other variables. Recommendations as to precise amounts are, therefore, not possible. In general, however, application to the locus to be protected of from 0.1 to 10.0 kilograms per hectare of the compound used in this invention will be satisfactory.

We claim:

1. A method for controlling unwanted fungi which comprises subjecting them to the action of an effective amount of a compound of the formula

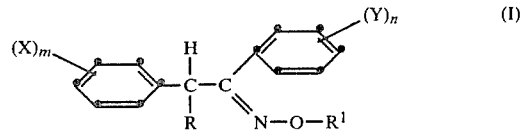

wherein:
(a) m is zero or one, n is one, X and Y each is middle halogen or alkyl of one to four carbon atoms bonded to a carbon atom in the meta- or para-position in the ring, R is methoxy and $R^1$ is hydrogen, methyl or acetyl;

(b) m, n, X and Y are as defined in (a), R is ethyl, and $R^1$ is hydrogen;

(c) m is one, n is zero, X is middle halogen, R is as defined in (a) and $R^1$ is hydrogen;

(d) m is one, X is as defined in (a), n is zero, R is as defined in (a) and $R^1$ is hydrogen, the compound being in the Z isomeric configuration; or (e) m is zero, n is zero or one, Y is as defined in (a), R is alkylthio of one or two carbon atoms and $R^1$ is hydrogen.

* * * * *